(12) United States Patent
Cheng

(10) Patent No.: US 7,097,655 B2
(45) Date of Patent: Aug. 29, 2006

(54) ELECTRIC HEAT THERAPY TECHNIQUE AND INSTRUMENT

(76) Inventor: Tzu-Chen Cheng, Av. 27 de Febrero, #418, Mirador Norte. POBox 165-2, Santo Domingo, D.N. (DO)

(*) Notice: Subject to any disclaimer, the term of this patent is extended or adjusted under 35 U.S.C. 154(b) by 253 days.

(21) Appl. No.: 10/347,099

(22) Filed: Jan. 17, 2003

(65) Prior Publication Data

US 2004/0143309 A1    Jul. 22, 2004

(51) Int. Cl.
*A61N 5/06* (2006.01)

(52) U.S. Cl. .................. 607/88; 606/1; 606/2; 128/898
(58) Field of Classification Search .................. 607/80, 607/108–111, 88, 90, 91, 92, 93; 362/19, 362/264, 294; 392/410, 409
See application file for complete search history.

(56) References Cited

U.S. PATENT DOCUMENTS

| 4,159,411 | A | * | 6/1979 | Ellersick ...................... 392/410 |
| 4,505,545 | A | * | 3/1985 | Salia-Munoz ............... 359/896 |
| 4,658,823 | A | * | 4/1987 | Beddoe et al. ................ 607/90 |
| 5,001,608 | A | * | 3/1991 | Kehrli et al. .................. 362/19 |

* cited by examiner

*Primary Examiner*—Rosiland Rollins
(74) *Attorney, Agent, or Firm*—Leong C. Lei

(57) ABSTRACT

An electric heat therapy instrument has an electric ampere controller 1 connected by two outside electric wires 2 to a 110-v electric outlet. The handle tube 3 is joined in its inferior extreme to a heating tube 9. A 110-v, 20-w bulb 6 is putting on the bulb socket 5 inside of the heating tube 9. To conserve the heating tube 9 temperature level and avoid the heat expansion to the handle tube 3, I invent a technique to cut the expansion of the heat in a metal material, it consists in making horizontal and round holes 7 around the top of the heating tube 9.

6 Claims, 2 Drawing Sheets

ELECTRIC HEAT THERAPY TECHNIQUE AND INSTRUMENT

CROSS-REFERENCE TO RELATED APPLICATION

Not Applicable

FEDERALLY SPONSERD RESERCH

Not applicable

SEQUENCE LISTING OR PROGRAM

Not applicable

1. Field of the Invention

This invention relates generally to heat therapy, including heat therapy technique and apparatus. The detailed specification is in the description of invention of page 3.

2. Prior Art

Historically, heat has been a natural remedy due to having effects to relieve pain and enhance the recovery process. By increasing the temperature of the skin surface and underlying tissues, heat stimulates the thermoreceptors—sensory receptors that respond to heat and cold—which then help block transmissions of pain signals to the brain. This translates into a significant decrease of discomfort. Heat therapy increases blood flow, which helps to decrease stiffness, relaxes sore muscles, and provides soothing comfort. Many thermotherapy techniques and instrument are based on hot water and hot air as heating medium, which are generated by hot pack, paraffin wax, therapeutic lamp, etc. Those instruments are unsatisfied by the human in the therapeutic operation.

SUMMARY OF THE INVENTION

The invention provides a remedied technique and apparatus based on heat therapy, which are more convenient, safety, effective and easy operation, because of its structure and heat conductive medium. This invented apparatus is comprised of a handle tube (in the middle portion of apparatus) a power source assembly (in the upper portion of apparatus) and a heat tube (in the lower portion of the apparatus). They are then combined into a vertical device with conjoining each other by the screw thread. In the inner of heating tube a light bulb sitting on a ceramic socket that is attached to the bottom of the handle tube by a turnbuckle. The bottom the handle tube has a round hole for the electrical cord from a ceramic electrical socket to the adjustable power controller.

DRAWINGS—FIGURES

DRAWINGS—REFERENCE NUMERALS

Figure 1:
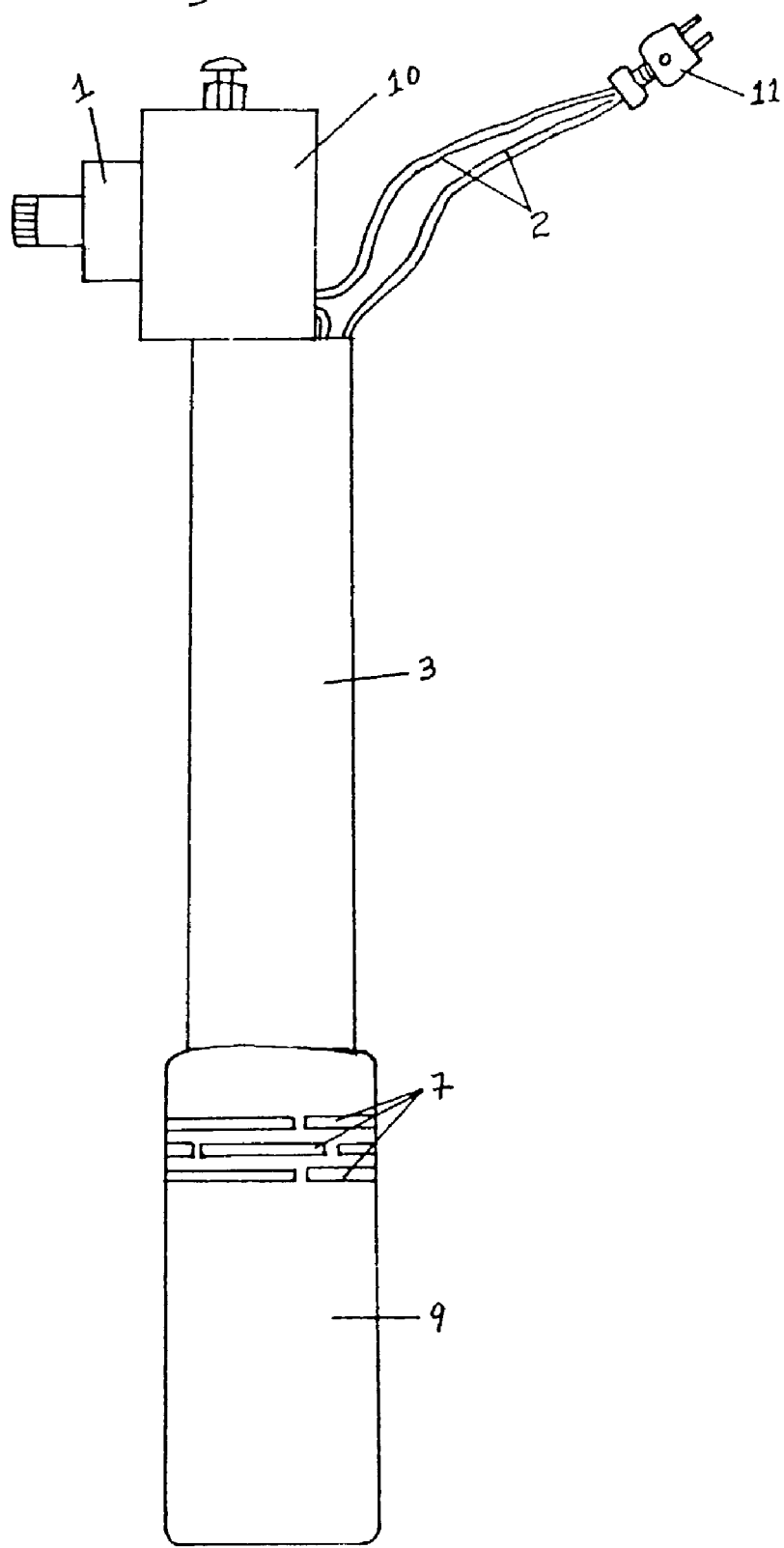
FIG. 1 illustrates the sectional elevation view of an embodiment of the therapeutic apparatus according to the invention.
Figure 2:
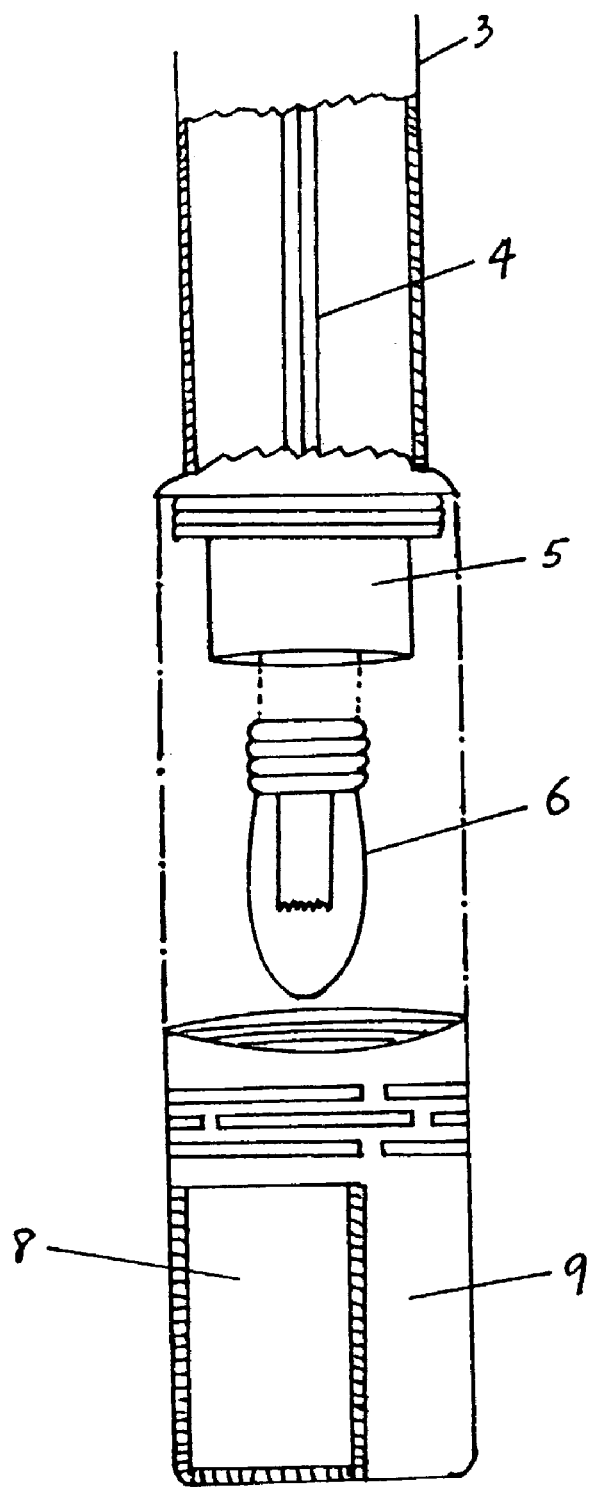
FIG. 2 shows the electric light bulb included in the apparatus.

1 Electric power controller
2 Two outside electric cord
3 Handle tube
4 Two inside electric cord
5 Bulb socket
6 15-w bulb
7 Horizontal slit holes
8 Heating room
9 Heat tube
10 Adjustable electric power controller case.
11 Electric plug

DESCRIPTION OF THE INVENTION

The Method

One can manage easily the apparatus. To handle the instrument, one holds handle tube 3, which is cold and safe to handle. The handle tube 3 joints to the heat tube 9, and by special design of this apparatus, the heat can't be conducted to the handle tube 3. One should cover the skin area with a piece of cloth to avoid direct contact with the heat tube 9, which is hot. One person using the apparatus can move the heat tube 9 directly to desired place. By pressing and relieving the heat tube 9, one can massage the problematic area to increase the temperature and comfort.

The invention advantaged apparatus has a best heat conductive tube, which is a heat tube 9 (a cylindrical metallic pipe), it is used a medium of the heat conduction from heating room 8 to the skin, while the bottom of heat tube is sealed, and its upper side has 3 horizontal slit holes 7 to avoid the heat from heat tube 9 conduction to handle tube 3. So that make a high temperature level in this portion of heat tube 9 and the other portion of handle tube 3 is cold. It is a great deal of difference with the other apparatus. The light bulb is inserted in the bulb socket 5 (ceramic socket), it is enveloped in the heating room 8, and has generated a higher temperature than an electric coil heater. The result shows as the following by a testing in same condition several times.

Light bulb→ in same heating room 8 ←electric coil heater (110 v, 15 watts) Same consumption in 0.12 amp (110 v, 15 watts)

Light Bulb (110 v, 15 Watts)

| Time passing From 0–80 minutes | Heat tube temperature | Increased temperature |
| --- | --- | --- |
| 0 | 28° C. | |
| 10 | 66° C. | 38° C. |
| 20 | 90° C. | 24° C. |
| 30 | 102° C. | 12° C. |
| 40 | 109° C. | 7° C. |
| 50 | 113° C. | 4° C. |
| 60 | 115° C. | 2° C. |
| 70 | 116° C. | 1° C. |
| 80 | 116° C. | 0° C. |

Electric Coil Heater (110 v, 15 Watts)

| Time passing From 0–80 minutes | Heat tube temperature | Increased temperature |
| --- | --- | --- |
| 0 | 28° C. | |
| 10 | 42° C. | 14° C. |
| 20 | 64° C. | 22° C. |
| 30 | 80° C. | 16° C. |
| 40 | 88° C. | 8° C. |
| 50 | 91° C. | 3° C. |
| 60 | 93° C. | 2° C. |

| Time passing From 0–80 minutes | Heat tube temperature | Increased temperature |
| --- | --- | --- |
| 70 | 116° C. | 1° C. |
| 80 | 116° C. | 0° C. |

Conclusion: The light bulb is better in safety, heating fast, easily to replace and producing higher energy.

According to prior-present thermometry, along my experience that is a precious temperature of the application of heat therapy.

1) Firstly one can use the apparatus to enhance body blood flow by massaging in internal side of the arms and the legs with the external wall of heat tube 9. Therefore getting a physical therapy in the whole body, so that it can be instead of any hardly exercise for the week people by a range of the showed temperature 66° C.–90° C. during 20–30 minutes, the temperature is safety by a piece of cloth to cover the skin and moving the apparatus in the meantime.

2) The other application consists in relieving muscular spam, treatment of pain and congestion due to injury, inflammation or infection. The therapeutic temperature would be higher in the range of 90° C.–100° C., during 5–10 minutes, the temperature is safety by a piece of cloth to cover the skin and moving the apparatus in the meantime, then one can profits an effect of the deep heat therapy from the training tissue anti-heat during day by day.

Structure

The electric heat therapy apparatus has an adjustable electric power controller 1, connecting with two outside electric cords 2. The adjustable power controller is located in a case 10 in the top of the handle tube 3. Two inside electric cords 4 putting inside of the handle tube 3 are protected by a heat shrinkable product resisting 180° C. it is connected from, connects the light electric power controller to a ceramic bulb socket 5. A 110 v, 15 watts bulb 6 is putting on the ceramic bulb socket 5. The bulb produces high heat in the heating room 8 and heats the heat tube 9. To conserve the heat tube 9 temperature level and avoid the heat conduction to the handle tube 3, I invent a method to prevent the conduction of the heat in a metal material, it consists in making 3 horizontal slit holes 7 around the top of the heat tube 9.

I claim:

1. A method of heat therapy applied to human skin by use of an apparatus comprising a heat tube, comprising the steps of:

covering the human skin area with a piece of cloth;
heating the heat tube of the apparatus, wherein the heat tube is heat conductive;
pressing the heated heat tube of the apparatus onto the cloth to transmit the heat to the underlying tissues or surface of the afflicted human skin area;
moving the heated tube on the cloth to control the temperature of the skin area and to increase the human skin area that is heated by the heat tube;
wherein the apparatus comprises a case, a handle tube and the heat tube; the case is adjoined to the top of the handle tube; the handle tube is adjoined to the top of the heat tube; the case encloses an adjustable electric power controller to be connected to an electric power source; the handle tube encloses an electric light bulb connected to the adjustable electric power controller; the heat tube comprises a plurality of slits adjacent to the handle tube to prevent heat conduction to the handle tube from the wall of the heat tube.

2. The method of claim 1 to increase blood flow, relieve muscular spasm, treat pain, treat swelling, or treat infection of the human skin area.

3. The method of claim 1 wherein the heat tube has nine slits.

4. The method of claim 1 wherein the heat tube is a metal.

5. The method of claim 1 wherein the heat tube is stainless steel.

6. The method of claim 1 wherein the electric light bulb is a 110-v, 20-w bulb.

* * * * *